(12) United States Patent
D'Silva

(10) Patent No.: US 7,457,685 B2
(45) Date of Patent: Nov. 25, 2008

(54) PREPARING FOR INDIVIDUALIZED DOSAGE FORMS OF MEDICAMENTS

(76) Inventor: Joe D'Silva, 753 Shearer St., North Wales, PA (US) 19454

( * ) Notice: Subject to any disclaimer, the term of this patent is extended or adjusted under 35 U.S.C. 154(b) by 246 days.

(21) Appl. No.: 10/578,120

(22) PCT Filed: Nov. 18, 2004

(86) PCT No.: PCT/US2004/038868

§ 371 (c)(1),
(2), (4) Date: May 1, 2006

(87) PCT Pub. No.: WO2005/053608

PCT Pub. Date: Jun. 16, 2005

(65) Prior Publication Data

US 2007/0068959 A1    Mar. 29, 2007

Related U.S. Application Data

(60) Provisional application No. 60/525,276, filed on Nov. 26, 2003.

(51) Int. Cl.
*G06F 17/00* (2006.01)
(52) U.S. Cl. .................. 700/239; 700/233; 700/240
(58) Field of Classification Search ................ 700/239
See application file for complete search history.

(56) References Cited

U.S. PATENT DOCUMENTS

| 3,554,412 | A | * | 1/1971 | Hayashi et al. | ............. 222/346 |
| 4,712,511 | A | * | 12/1987 | Zamzow et al. | .......... 119/51.02 |
| 5,176,285 | A | | 1/1993 | Shaw | |
| 5,672,154 | A | * | 9/1997 | Sillen et al. | ................. 706/924 |
| 5,853,244 | A | * | 12/1998 | Hoff et al. | .................... 700/265 |
| 6,286,567 | B1 | * | 9/2001 | Runft | ......................... 141/145 |
| 6,497,342 | B2 | | 12/2002 | Zhang et al. | |
| 7,295,889 | B2 | * | 11/2007 | Lahteenmaki | ............... 700/239 |

* cited by examiner

*Primary Examiner*—Gene Crawford
*Assistant Examiner*—Timothy R Waggoner
(74) *Attorney, Agent, or Firm*—Connolly Bove Lodge & Hutz; Christine M. Hansen

(57) ABSTRACT

The invention relates to methods for preparing individualized dosage forms of medicines, vitamins, mineral supplements and nutraceuticals in capsule or liquid form. The invention also relates to a system for preparing individualized dosage forms in which a processor is configured to identify a medicament formulation for an individual patient's dosaging needs and communicates this formulation information to a dispensing station where a capsule or a formulation of pellets of small diameter size for reconstitution into a liquid or semi-solid is formed that is specific to the individual's dosaging needs.

23 Claims, 2 Drawing Sheets

PREPARING FOR INDIVIDUALIZED DOSAGE FORMS OF MEDICAMENTS

RELATED APPLICATIONS

This application is a national stage application (under 35 U.S.C. 371) of PCT/US2004/038868 filed Nov. 18, 2004 which claims benefit to U.S. provisional application 60/525,276, filed Nov. 26, 2003.

FIELD OF INVENTION

The invention relates to methods for preparing individualized dosage forms of medicines, vitamins, mineral supplements and nutraceuticals in capsule or liquid form. The invention also relates to a system for preparing individualized dosage forms in which a processor is configured to identify a medicament formulation for an individual patient's dosaging needs and communicates this formulation information to a dispensing station where a capsule or a formulation of pellets of small diameter size for reconstitution into a liquid or semisolid is formed that is specific to the individual's dosaging needs.

BACKGROUND OF INVENTION

Many human patients, especially the elderly, require the administration of several oral medications at various times during the day. The number and type of medications vary depending on the medical conditions under treatment. It is not unusual to have four to six tablets and capsules prescribed per dosing time. Often, the number and type of tablets and capsules for dosing varies depending upon the time of day. The need to ensure proper allocation of the medications is critical. The patient, a caregiver or a healthcare provider has to carefully allocate various tablets and capsules and ensure that the patient ingests the entire allocation at the correct time. Misallocation will cause sub par dosing or overdosing that may lead to undesirable results.

The allocation process can be undertaken at each dosing time. Alternatively, the allocations may be undertaken in advance. Often a storage container with several labeled compartments is used. The tablets and capsules required for a particular day and dosing time are placed within a compartment labeled with that day (e.g., Monday, Tuesday, etc.) and with the time of day for the administration (e.g., before breakfast, with breakfast, with lunch, etc.). The patient then takes, or is administered, the contents of the designated compartment at the appropriate dosing time.

The system described above has several disadvantages. First, the accurate allocation of the tablets and capsules is dependant on the skill and focus of the person undertaking the process. An elderly patient may have problems with eyesight and lack of concentration, leading to misallocation of the medications. If the process is undertaken in haste, there is a potential for medications to become mixed up. The process is made further difficult because the physical appearances of many tablets and capsules are similar and in some cases close to identical. Inaccurate allocation of medications may have serious consequences. For example, a patient may inadvertently be overdosed, leading to harmful side effects, or be under-dosed, leading to sub-optimal treatment.

A second disadvantage of manual tablet and capsule allocation by the user or a caregiver is the inconvenience and physical discomfort to the patient of administering multiple tablets and capsules at a dosing time. For example, for elderly patients and those afflicted with diseases such as Alzheimer's or Parkinson's syndrome, the process of swallowing several tablets or capsules at a single dosing time is a tedious and difficult process.

Commercial machines presently available allow for the semi-automatic allocation of tablets and capsules required by a patient for a particular dosing time. However, such machines are usually designed for internal use within hospitals and other well-controlled healthcare environments. The machines often involve expensive capital equipment that must be purchased by the caregiver or the institution caring for a patient. An example of such a machine is the SafetyPak™ system marketed by the Omnicell Corporation for use in hospitals. The machine repackages tablets and capsules into unit-dose packages (such as blister packs) with barcodes. Patient medication bins are stocked with the unit-dose packages. Nurses and other caregivers administer the medications to patients. Stationary and portable readers allow for the tracking and verification of the packaged medications via evaluation of the barcodes. The barcodes help to ensure that the correct prescribed medications are administered to each patient. Such a system has certain disadvantages. The process involves the repackaging of tablets and capsules and the additional costs associated with such operations. When multiple medications are to be administered, the use of this system necessitates the opening of several packages at each dosing time, which may be difficult for elderly patients or other patients with difficulty opening packages. Also, opening multiple medications is time-consuming for a care-giver in a hospital or assisted living facility.

The present invention solves these problems by providing to each patient several medications required for a single dosing time in a few, but preferably one, capsules. For each dosing time, the capsules are provided in a single sealed container or sachet labeled with the patient's name, the encapsulated medications and their dose, the date for administration, the dosing time and a bar code. The bar code provides a link to a database on the encapsulated medications including identity, dose and details of manufacture of the capsules. At the requisite dosing time, the capsules are administered to the patient with an appropriate amount of fluid.

Another problem with administering medications concerns those patients, both human and veterinary, for whom the use of tablets and capsules is not feasible. Some patients are unable to ingest tablets and capsules in a single and smooth swallowing motion, or lack the desire to ingest such dosage forms. Also, some tablets and capsules have an unpleasant taste or an uncomfortable or unpleasant size. Patients who experience such problems include the elderly, particularly those in assisted living facilities, pediatric patients and patients who have encountered severe trauma due to surgery or involvement in accidents. Also, animals often will not, or cannot, swallow tablets or capsules. In such situations, health care providers desire alternative dosage forms, especially liquids or a semi-solid. For many medications, however, liquid formulations are not commercially available. Such formulations then must be made on an ad hoc basis by using a device such as a mortar and pestle to grind a tablet into particles and then dispersing it in a liquid or semi-solid such as applesauce.

A second objective of the present invention is to solve these problems by providing to each patient one or several medications required for a single dosing time in a sealed container ready for reconstitution into a flavored liquid or semisolid product for oral administration. Flavors, sweeteners and viscosity enhancers accompany the medications in the sealed container. The selection of the flavors, sweeteners and viscosity enhancers is based on each individual patient's preference. When necessary, buffering agents may be added for proper pH control and antioxidants added to prevent oxidative decomposition. The container is labeled with the patient's name, the medications and their dose, flavors, sweeteners, viscosity enhancers, buffering agents and antioxidants where applicable, the date for administration and the dosing time, instructions for reconstitution and a bar code. The bar code provides a link to a database on the medications, flavors, sweeteners, and viscosity enhancers and where applicable buffering agents and antioxidants including identity, dose and details of manufacture. At the appropriate dosing time, the requisite amount of liquid is added to the bottle and the contents agitated to produce a liquid or semi-solid formulation. The formulation is then administered to the patient.

A third problem with the administration of medicines and nutritional supplements is the difficulty in providing optimum dosage amounts because only a limited number of tablet or capsule strengths of a particular medicament are available. In many instances, physicians would like to have the option of easily adjusting the dosage of oral medications based on physiological factors, but are constrained to the dosage amounts allowed by combining available tablet or capsule strengths. This is especially true for human patients who are severely ill, have altered metabolic rates or have other high risk factors and those requiring administration of medications with low therapeutic indices such as oncology, cardiac and bronchodilator drug regimens.

In some instances, the availability of tablets and capsules of varying strengths can provide a partial solution to the problem. A combination of such tablets can provide a dose that is close to the desired target value. Another approach is to physically subdivide tablets by cutting or breaking them. The subdivided tablets can be administered alone or combined with whole tablets to provide a dose that is close to the desired value. These approaches have some inherent disadvantages. It is difficult to provide the exact desired dose to the patient without the availability of tablets or capsules with a large number of varying strengths. Often tablets and capsules with such a range of strengths are not available. The subdivision of tablets is both difficult and inaccurate. The subdivision of the contents of capsules involves the removal and allocation of fine powders. The process is difficult and has the potential for resulting in major inaccuracies. Therefore the approaches do not offer physicians and healthcare providers with easy and accurate techniques to provide the exact dose desired for each patient.

Veterinarians would also like to have the option of being able to prescribe a broad range of dosage amounts. Veterinary patients vary widely in body weight. There is a wide variation in the weights of animals maintained as pets such as dogs, cats, guinea pigs and hamsters.

Variations in weights occur among and within the species. Many present commercial products cannot easily accommodate the medication dosages required by such variations.

A third objective of the present invention is to solve these problems by providing a method and system for preparing individualized dosage forms of a single or multiple medications that alone or in integral multiples provide a desired dosage for an individual patient. The individualized dosage forms may be made in an extremely wide variety of strengths. The dosage forms are preferably capsules filled with pellets. The capsules required for a single dosing time are provided in a sealed container or sachet. Alternatively, the doses can be provided in bottles along with flavors, sweeteners and viscosity enhancers for reconstitution into liquid or semi-solid formulations. The selection of the flavors and viscosity enhancers is based on each individual patient's preference. When necessary, buffering agents may be added for proper pH control, antioxidants added to prevent oxidative decomposition, and other excipients added to control dissolution, stability, etc.

Each capsule container or bottle with material for reconstitution is labeled with the patient's name, the medications and their dose, flavors, sweeteners, viscosity enhancers, buffering agents and antioxidants where applicable, the date of administration and dosing time, instructions for administration and a bar code. The bar code provides a link to a database on the medications, flavors and viscosity enhancers and where applicable, buffering agents and antioxidants including identity, dose and details of manufacture. At the requisite dosing time, the capsules are administered with an appropriate amount of fluid. Alternatively for products for reconstitution, the requisite amount of liquid is added to the bottle and the contents agitated to produce a liquid or semi-solid formulation for administration.

For human patients, the first, second and third objectives provide advantages to patients in residential homes, assisted living facilities, hospices and hospitals and to their healthcare providers. The second and third objectives also provide advantages for the veterinarians and healthcare providers who care for animal patients such as pets, equines and zoo animals.

In many instances, human consumers taking vitamins, mineral supplements or nutraceutical products would like to select their individual doses based on advice from healthcare professionals and their own personal preferences. Present commercial products such as multivitamin tablets do not easily make available such choices to patients.

A fourth objective of the invention is to solve this problem by providing combinations of specific doses of vitamins, mineral supplements or nutraceutical products to human consumers based on individual preferences. The vitamins, mineral supplements or nutraceutical products can be provided in capsules. The capsules required for a single dosing time are provided in a sealed container or sachet. Alternatively, the materials can be provided in bottles along with flavors, sweeteners and viscosity enhancers for reconstitution into liquid or semi-solid formulations. The selection of the flavors and viscosity enhancers is based on each individual patient's preference. When necessary, buffering agents may be added for proper pH control and antioxidants to prevent oxidative decomposition. Each capsule container or bottle with material for reconstitution is labeled with the patient's name, the vitamins, mineral supplements, nutraceutical products, flavors, sweeteners, viscosity enhancers or buffering agents where applicable, and their dose, the date and dosing time, instructions for administration and a bar code. The bar code provides a link to a database on the vitamins, mineral supplements or nutraceutical products and the flavors and viscosity enhancers and where applicable, buffering agents and antioxidants including identity, dose and details of manufacture. At the requisite dosing time, the capsules are administered with an appropriate amount of fluid. Alternatively, for products for reconstitution, the requisite amount of liquid is added to the bottle and the contents agitated to produce a liquid or semi-solid formulation for administration.

The invention described herein provides the following advantages over present practices:

1. An easy and convenient solution for providing multiple oral medications, vitamins, mineral supplements or nutraceutical products either in one capsule or in integral multiples of that one capsule or in one container ready for reconstitution into flavored liquid or semi-solid formulations.

2. The number of capsules for administration represents in many cases a reduction in number from the corresponding number of commercial tablets and capsules that would be required if each medicament was administered separately.
3. The doses of each medicament can be readily adjusted for physiological parameters.
4. An easily accessible manufacturing record is maintained of the complete composition of each dosage form.
5. The products for reconstitution into liquid or semi-solid formulations can be supplied with sweeteners, flavors and viscosity enhancing agents based on the preference of the patient.
6. When needed, buffers and antioxidants are included to provide for optimum stability of the liquid or semi-solid products.
7. The invention can be used both for human and veterinary patients.

BRIEF SUMMARY OF INVENTION

The invention relates to a method to prepare an individualized dosage form of a medicament, the method comprising receiving information identifying for an individual patient the medicament and a desired dosage amount at a dosage time of the medicament desired for therapeutic effect; selecting at least two pellets comprising the medicament; and combining the pellets into a single capsule to prepare an individualized dosage form that alone or in integral multiples provides the desired dosage amount for the individual patient at the dosage time.

The invention also relates to a method to prepare an individualized dosage form of a medicament for reconstitution into a liquid, the method comprising receiving information identifying for an individual patient the medicament and a desired dosage amount at a dosage time of the medicament desired for therapeutic effect; selecting pellets comprising the medicament and an excipient, wherein if the medicament and the excipient are contained in one pellet, at least two pellets that are selected and if the medicament and the excipient are contained in separate pellets, at least one medicament pellet and at least one excipient pellet are selected, and the pellets are dispersible in the liquid at room temperature with agitation; combining the pellets into a single container to prepare an individualized dosage form that provides the desired dosage amount for the individual patient at the dosage time; and packaging the single container with instructions to add the liquid to the contents of the single container sufficient to prepare a liquid individualized dosage form.

The invention also concerns the formulations produced by the methods of the invention.

The invention also concerns a system for preparing an individualized dosage form comprising:
(a) a first database stored on a computer readable medium having data records associated with an individual patient and containing information on a medicament, its desired dosage amount and dosage time for the individual patient;
(b) a second database stored on a computer readable medium having data records associated with a manufacturing inventory of medicaments, excipients and packaging material;
(c) a third database stored on a computer readable medium having data records associated with capsule formulations of pellets, the pellets comprised of medicaments and excipients;
(d) a processor associated with the first, second and third databases that is configured to identify a capsule formulation of pellets that alone or in integral multiples provides the desired dosage amount for the individual patient at the dosage time and that is further configured to identify manufacturing inventory needed to prepare the capsule formulation;
(e) a mechanical transport system that is in communication with the processor and that, in response to communication from the processor on the manufacturing inventory needed to prepare the capsule formulation, transports the identified manufacturing inventory from a storage area; and
(f) a dispensing station that receives the identified manufacturing inventory from the mechanical transport system, wherein the dispensing station is in communication with the processor such that information on the capsule formulation is received by the dispensing station and the dispensing station dispenses pellets into a capsule body in a quantity and amount such that an individualized dosage form that alone or in integral multiples provides the desired dosage amount of the medicament for the individual patient at a single dosage time is prepared.

The invention also concerns a system for preparing an individualized dosage form for reconstitution into a liquid comprising:
(a) a first database stored on a computer readable medium having data records associated with an individual patient and containing information on a medicament, its desired dosage amount and dosage time for the individual patient;
(b) a second database stored on a computer readable medium having data records associated with manufacturing inventory of medicaments, excipients and packaging materials;
(c) a third database stored on a computer readable medium having data records associated with formulations of pellets for reconstitution in the liquid, the pellets comprised of medicaments and excipients;
(d) a processor associated with the first, second and third databases that is configured to identify a formulation of pellets for reconstitution in the liquid that provides the desired dosage amount for the individual patient at the dosage time and that is further configured to identify manufacturing inventory needed to prepare the formulation;
(e) a mechanical transport system that is in communication with the processor and that, in response to communication from the processor on the manufacturing inventory needed to prepare the formulation, transports the identified manufacturing inventory from a storage area; and
(f) a dispensing station that receives the identified manufacturing inventory from the mechanical transport system, wherein the dispensing station is in communication with the processor such that information on the formulation is received by the dispensing station and the dispensing station dispenses pellets into a single container in a quantity and amount such that an individualized dosage form that provides the desired dosage amount of the medicament for the individual patient at the single dosage time is prepared; and
(g) a consolidating station in communication with the processor that receives the single container comprising the individualized dosage form and packages the container with written instructions to add the liquid to the contents of the single container sufficient to prepare a liquid individualized dosage form.

Preferably, the systems of the invention also comprise one or more verification stations in communication with the processor that analyzes the individualized dosage form to verify that the form contains desired components. The verification station may include (i) a balance; (ii) a dosage color profile analyzer for reflectance spectroscopy; or (iii) both a balance and a dosage color profile analyzer for reflectance spectroscopy.

BRIEF DESCRIPTION OF DRAWINGS

FIG. 1 depicts a storage container for the pellet formulation (1), a coupling device (2), an adapter containing a filling device (3), the pellet formulation (4), a capsule body or a bottle (5) and an electronic balance (6).

FIG. 2 depicts the central computer control system in communication with first, second, and third databases and the processor associated with the first, second and third databases (7), data transmission systems (8), storage and dispensing system for capsules, bottles, sachets and storage containers (9), robotic mechanical transportation for moving capsules, bottles, sachets and storage containers (10), a series of dispensing and verification stations with a robotic mechanical transportation system (11) and consolidating stations for assembly of the final shipments (12).

DETAILED DESCRIPTION OF INVENTION

Figure 1:
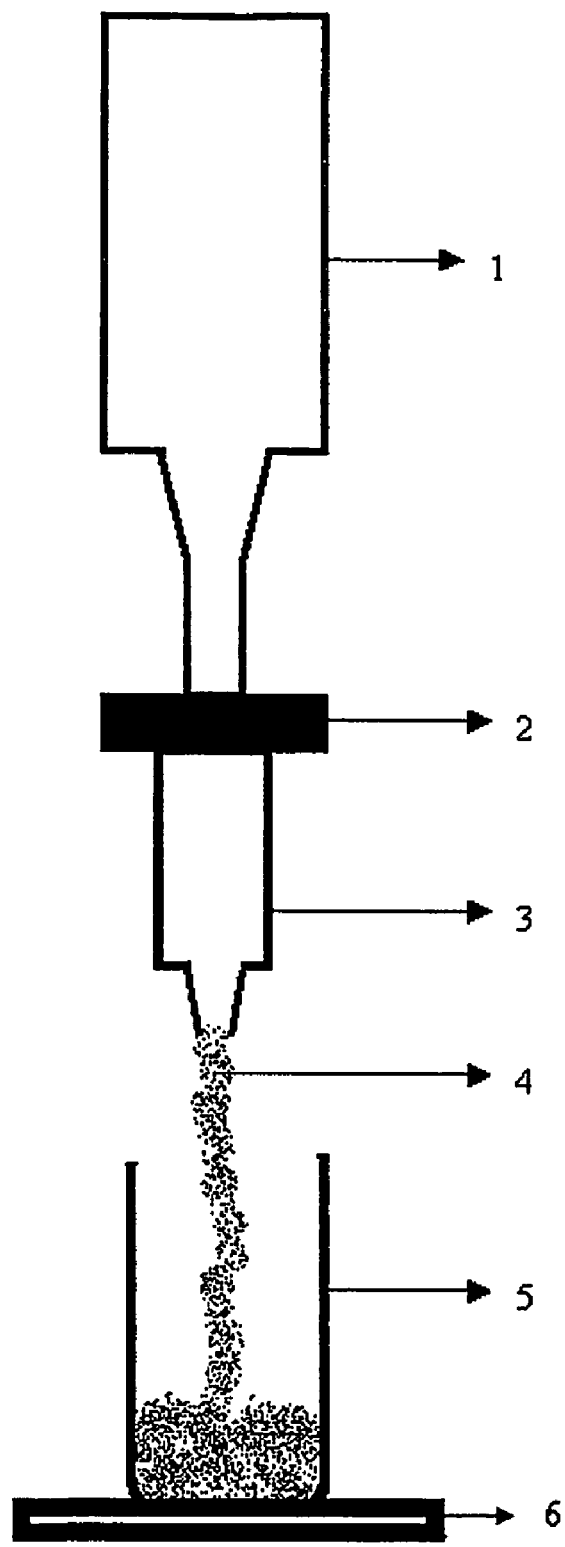
FIG. 1: Cross section of the construction of the dispensing station according to the invention.

The invention concerns methods for preparing individualized dosage forms made of individual pellets. A single pellet preferably contains either a medicament or an excipient. As used herein, "medicament" includes a medication, vitamin, nutrient, mineral supplement, nutraceutical, or pharmaceutical product. "Excipient" refers to pharmaceutically acceptable excipients as known to those of skill in the art. "Excipient" includes for example flavors, sweeteners, viscosity enhancers, buffering agents, fillers, stabilizers, and antioxidants.

As used herein, "dosing time" or "dosaging time" refers to a particular time when one dosage of a medicament is to be administered. The dosing time may be repeated at regular intervals, such as when one medicament is dosed once daily at the same time for two weeks. Such a regular, repeated dosage time may be referred to as a single dosage time or a single dosing time. The invention is directed to human and animal patients, preferably mammals. "Packaging materials" refers to capsule bodies, containers and other materials for containing or packaging a pellet formulation.

In a preferred embodiment, the formulations consist of two parts. One part consists of coated free flowing pellets containing a single or multiple medicaments. In aqueous environments the coatings gradually erode exposing the medicament to the disintegration and dissolution processes. The second part of the formulations consists of coated free flowing pellets containing excipients, such as flavors, sweeteners, viscosity enhancers, buffering agents or antioxidants. A single pellet may contain one or multiple excipients. In aqueous environments the excipient pellets dissolve rapidly to release the excipients.

In one embodiment of the invention, the method of preparing an individualized dosage form of a medicament in one or more capsules, at least two pellets are selected and at least one pellet comprises a medicament and at least one pellet comprises an excipient. Preferably, more than two pellets are selected and, and still more preferably more than five are selected.

The manufacturing system of the invention consists of an automated metering and transportation system that is controlled by a computer. The system is capable of accurately allocating various amounts of the pellets and packaging them into capsules or into a bottle in a dispensing station. The system preferably has a verification station that verifies the accuracy of the manufacturing process and is connected to a database in which is stored electronic records of each manufacturing step. Manufacturing of products containing prescription medications is undertaken upon the receipt of the orders of a licensed physician. Manufacturing of products containing over-the-counter medications, vitamins, mineral supplements or nutraceuticals are undertaken upon receipt of a request from a consumer.

The manufacturing process provides patients and consumers with several dosing options: solid capsules or liquid or semi-soft formulations. Preferably, all the capsules destined for a particular dosing time for a patient are placed in a sealed container or sachet. At each dosing time, the appropriate container is opened and the capsules are administered to the patient or consumer along with a suitable quantity of a liquid. Alternatively, pellets containing the desired dosage of medicament for a dosing time for a particular individual patient are combined with pellets have desired excipients for a liquid formulation into a single package such as a bottle. Each bottle is sealed. At the desired dosing time, the bottle is opened and a prescribed amount of liquid is added to the contents. The contents are then agitated to produce a liquid or semi-solid for oral administration.

The manufactured products are labeled and tracked by a system. Each sealed container is labeled with the name of the patient, details of the medication or vitamin or mineral supplement or nutraceutical or flavor or sweetener or viscosity enhancer or buffering agent contents, the date, time and instructions for administration and a code, preferably a machine readable code such as a bar code. The code is associated in a manufacturing database with details of the manufacture of that particular dosage form. The dosage forms for an appropriate number of dosing times are packaged in a single shipment for transportation to the patient. Preferably, medications required for several days' therapy are provided in one shipment package. Shipments may be delivered to patients at any location including their residences, hospitals and assisted living facilities.

The invention is designed to provide each individual patient or consumer with a choice of the following products:

1. All or a majority of their oral medications for a particular dosing time contained in one or few capsules. The dose of each individual medication can be adjusted for physiological parameters.
2. All or a majority of their oral medications for a particular dosing time contained in a bottle along with suitable flavors, sweeteners, viscosity enhancers and where needed, buffers and antioxidants. The materials are in the form of pellets. The contents can be transformed into a liquid or semi-solid product by the addition of a liquid. The dose of each medication can be adjusted for physiological parameters.
3. All or a majority of their vitamins, mineral supplements or nutraceuticals for a particular dosing time contained in one or a few capsules. The dose of each vitamin and mineral supplement can be adjusted for patient needs.
4. All or a majority of their vitamins, mineral supplements or nutraceuticals for a particular dosing time contained in a bottle along with suitable flavors, sweeteners, viscosity enhancers and where needed, buffers and antioxidants. The contents can be transformed into a liquid or semi-solid product by the addition of a liquid. The dose of each vitamin and mineral supplement can be adjusted for patient needs.

The invention provides the following advantages:

1. The invention provides each patient or consumer an individualized combination of medications or vitamins or mineral supplements or nutraceuticals, or combinations thereof. Each dosage unit is designed to meet the individual physiological needs of a patient at a particular dosing time. This feature of the invention provides each patient or consumer with optimized therapeutic benefits.
2. The invention provides each patient or consumer with a unique combination of medications or vitamins or mineral supplements or nutraceuticals either packaged in capsules or in containers for reconstitution into flavored oral liquids or semisolid products. This feature of the invention provides patients, consumers and healthcare workers with an easily accessed option for optimum product administration. The proper administration of the product provides each patient or consumer with optimized therapeutic benefits. The availability of capsule or liquid or semisolid product options assists healthcare providers in the proper administration of medicaments.
3. The invention provides each patient or consumer with multiple medications in a fewer number of capsules compared to the corresponding single entity commercial tablets or capsules. This feature of the invention provides patients, consumers and healthcare workers with a more convenient and facile option for administration of the medications or vitamins or mineral supplements or nutraceuticals. The proper administration of the product provides each patient or consumer with optimized therapeutic benefits by enhancing patient compliance and decreasing medication errors. The feature assists healthcare providers in the proper administration of medications or vitamins or mineral supplements or nutraceuticals.
4. Following the invention, individualized dosage forms can be manufactured in an automated and controlled fashion with a unique label for the products for each dosing time. The accuracy of the manufacturing process can be verified by maintaining an electronic record of the composition and manufacture of each dosage unit linked to a unique bar code. This feature of the invention provides patients, consumers and healthcare providers with a facile process for ensuring that all of the required medications or vitamins or mineral supplements or nutraceuticals are administered at the appropriate dosing time. The feature allows for the manufacture and quality control of such products in a cost-effective fashion. The feature provides healthcare providers and quality assurance personnel with the ability to rapidly and effectively track the composition and manufacturing characteristics of a dosage form. The feature aids in the conductance of a rapid response and investigation if any untoward effects are caused by the administration of one of the dosage forms.

There are two formulation components to the invention.

The first formulation component consists of free flowing pellets containing a single or multiple medicaments. Preferably, each pellet contains one medicament. The pellets may contain additional inert materials as required. The inert materials may include diluents such as lactose, binders such as microcrystalline cellulose and disintegrants such as modified starches.

The second formulation component consists of free flowing pellets containing one or more excipients such as flavors or sweeteners or viscosity enhancers, buffering agents, fillers, binders, or antioxidants. The pellets may contain one or a combination of these entities.

Both the medicament pellets and the excipient pellets are coated with a functional coating consisting of materials such as modified celluloses and sucrose. The functional coating may contain a suitable coloring of a specific hue. The functional coating of the excipient pellets may also contain disintegrants such as modified starches. The functional coating serves four purposes. The first purpose is to provide the contained medicament or excipient with a protective barrier resulting in adequate physical and chemical protection. The pellets will come into intimate contact when placed together in a capsule or bottle. The functional coating prevents the physical contact of two medicaments or excipients and thus prevents any detrimental stability effects. The second purpose of the functional coating is to provide the pellets with free flowing characteristics to facilitate the manufacture and assembly of the dosage forms.

The third purpose of the coating is to provide selective access by an aqueous environment to the contents of the pellet formulation. The coating design may restrict access of the aqueous environment to an extent of time of up to five to ten minutes. Subsequently, the degradation of the coating allows for the aqueous environment to disintegrate the pellet formulation and initiate the dissolution process for the medicaments or excipients. The ability of the coating to maintain its physical integrity for a definite period of time allows for the use of the pellet formulations in the manufacture of both capsules and products designed for reconstitution into liquids or semisolids formulations. In one embodiment, the medicament pellets are coated as to inhibit the instantaneous dissolution of medicaments. Thus the taste and smell of the resultant liquid products are less likely to be affected by the medicaments and more controlled by the added flavors and sweeteners, which preferably have a coating that is more quickly dissolved. However, the inhibition of the coating degradation process being selected for a relatively short period of time is not a detriment to the ultimate disintegration of the pellets and the resultant dissolution of the medicaments or vitamins or mineral supplements or nutraceuticals and absorption thereof. Preferably, the excipient pellet coating is such that upon coming into contact with an aqueous environment, the functional coating erodes immediately and thereby rapidly allows the pellets to disintegrate and release the contained flavors, sweeteners, viscosity enhancers and buffering agents, for example.

The fourth purpose of the coating is to provide a unique color pattern for one type of verification of the accuracy of the manufacturing process. When several pellets are combined into one formulation, the formulation will display a specific color pattern. The specific color pattern will be a proportional composite resulting from the colors of the individual pellets employed to make the combined product.

The size of the pellets is not greater than 1 mm in average diameter, preferably is between 50 to 2000 µm, and more preferably is between 100 and 1000 µm. The coated pellets can be manufactured using a combination of a variety of well known techniques for the formation and coating of the pellets. The techniques include compression, extrusion, spray drying, spray congealing, fluid bed coating and pan coating.

The viscosity enhancing agents contained in the excipient pellet formulation are generally polymers, which upon contact with the aqueous environment provide the product with a desirable viscosity. For some patients, a liquid product with very low viscosity characteristics may not be a desirable option. A product with the consistency of a "pudding" may be easier to ingest, in particular for the elderly patient population. The option of producing products with low or enhanced viscosity can be maintained by making available pellets with varying levels of polymeric agents. In one preferred embodiment of the invention, the polymers added to the product provide the formulation with a thixotropic nature. In such a formulation, the viscosity of the product increases upon standing to provide the desired physical stability and thus maintain the homogeneity of the product. Upon providing energy input to the product via shaking, the viscosity of the product is reduced allowing for optimal dosing characteristics. In one embodiment, thickeners such as sodium carboxymethyl cellulose are added in amounts of from approximately 0.1% w/v to about 0.5% w/v of the final liquid composition, and preferably from about 0.15% w/v to about 0.25% w/v and most preferably in an amount of about 0.20% w/v of the total formulation.

When necessary, the pellets contain agents that control the pH of the liquid dosage product, such as buffers. The pellets may also contain antioxidant agents. The agents maintain the stability of the medicinal compounds within the final liquid or semisolid formulation by providing conditions under which the decomposition of the medicinal compound is minimized, and/or the destabilization of the formulation is avoided.

Many medicinal compounds possess unpleasant taste characteristics. The flavors and sweeteners contained in the pellets will assist in enhancing the palatability of the product. The flavors are selected to meet the requirements of specific patient populations. Suitable sweeteners for the compositions of the invention include water-soluble artificial sweeteners such as saccharin salts, cyclamate salts, acesulfame-K, monoammonium glycyrrhizinate and mixtures thereof. Other suitable sweetening agents include aspartame, sucrose, sucralose, protein based sweeteners such as thymidine, monellin and the like. In general, the effective amount of sweetener employed varies according to the type of sweetener used and the level of sweetness desired. Preferably, the amount is from about 0.01% w/v to about 5.0% w/v and more preferably from about 0.01% w/v to about 1.0% w/v of the liquid dosage formulation.

Sodium saccharin is a preferred sweetener and is incorporated in an amount of from about 0.01% w/v to about 0.5% w/v of the weight of the final liquid dosage formulation.

The flavorings that may be used in the invention include those known to the skilled artisan, such as natural and artificial flavors. More specifically, the flavorings may be synthetic flavor oils and flavoring aromatics, and/or oils, oleo resins and extracts derived from plants, leaves, flowers, and fruits and combinations thereof. Examples of suitable flavorings include spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almond. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, and apricot. These flavorings may be used individually or in combinations with each other. Preferred flavors include peppermint, menthol, artificial vanilla, cinnamon derivatives, and various fruit flavors.

Flavorings such as aldehydes and esters including cinnamyl acetate, cinnamaldehyde, citral, diethylacetal, dihydrocarvyl acetate, eugenyl formate, and p-methylanisole may also be used. Generally, any flavoring or food additive described in "Chemicals Used in Food Processing" pub. 1274 by the National Academy of Sciences, pages 63-258 may be used.

Further examples of suitable aldehyde flavorings include acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); alpha-amyl cinnamaldehyde (spicy fruity flavors); butyraldehyde (butter, cheese); valeraldehyde (butter, cheese); citronella (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2,6-dimethyloctanal (green fruit); 2-dodecenal (citrus, mandarin); cherry; grape; and mixtures thereof. The amount of flavoring employed is normally a matter of preference subject to such factors as flavor type, individual flavor, and strength desired. Generally, flavors in amounts of about 0.05% to about 2.0% by weight of the total liquid dosage formulation are suitable and amounts of about 0.05% to 1.5% are preferred.

For veterinary products, flavorings appealing to the animal patient are desirable. An example is 3,7-dimethyl-1,6-octadien-3-ol (commonly known as "linalool"), preferably in an amount of between about 0.0001 to 0.001% by weight of the liquid dosage product, as disclosed in U.S. Pat. No. 4,294,857 to Fuller issued Oct. 13, 1981. Additional flavorings are disclosed in Furia et al., "Fenaroli's Handbook of Flavor Ingredients", CRC Press. Other examples of suitable veterinary flavorings are: anise, bacon, caramel, celery, cheese, clover, fish flavors such as salmon, sardine and tuna, fish oils, fruit flavors such as apples, banana, cherry, raspberry and strawberry, garlic, lemon oil, licorice, liver, meat flavors such as beef, chicken and lamb, molasses, onion, parsley, peanut butter, milk powder, tomato, and vanillin.

Preferably, the liquid or semisolid dosage product reconstituted from the pellet formulations comprises one or more of the following:

(1) a medicament
(2) sweeteners such as sucrose, aspartame or saccharin
(3) buffering agents such as citrate, phosphate or acetate
(4) appropriate flavors, both natural and artificial
(5) viscosity enhancers such as hydroxypropyl cellulose, hydroxypropyl methylcellulose, xanthan gum or sodium carboxymethyl cellulose
(6) antioxidants such as propyl gallate or sodium metabisulfite, and
(7) water.

The individualized dosage forms for reconstitution in a liquid may be reconstituted in any of the liquids or semi-solid foods known to those of skill in the art as acceptable carriers for medicaments, and preferably is a liquid. For example, water, fruit juices, applesauce, and pudding may be used. Preferably, the liquid is water. Preferably, the liquid allows for ready reconstitution of the dosage form at room temperature with stirring or shaking.

In a preferred embodiment, each pellet formulation containing a medicament or excipient is packaged, stored and shipped in a single-use container to the facility for preparing individualized dosage forms. The container is preferably constructed of plastic. The container serves to protect, store and transport the pellet formulations to manufacturing facilities for further formulation into individualized dosage forms. At the manufacturing facility, the container (1) is opened and coupled with an adapter (3) through a coupling device (2) as shown in FIG. 1. The adapter contains a metering and filling device. The complete assembly forms a dispensing station capable of accurately metering out the pellet materials stored within the container (1). The pellets (4) are fed by the filling device through a narrow opening at the end of the dispensing station into a capsule or a bottle (5). The capsules or bottles are independently transported and positioned under a series of the dispensing stations and filled with the designated amount of each pellet formulation. Control of the filling sequence and the types and amount of the pellet formulations that are dispensed into a particular capsule or bottle are undertaken by a central computer system. Upon the completion of its designated filling cycle, the capsule or bottle contains a mixture of the required medicaments and excipients. The filling device contained in the adapter can be based on one or a combination of principles. The device could meter out the pellet formulations based on volumetric principles. Alternatively, the device could meter out the formulation by weight through a hinged or sliding door or similar opening and controlled by an electronic signal from a balance. The filling devices contained in the adaptors will be modifications of commercially marketed filling apparatuses. Examples of such devices are the auger fillers manufactured and sold by Matteer Burt or the vacuum and pressure method fillers manufactured and sold by M and O Perry Industries.

Figure 2:
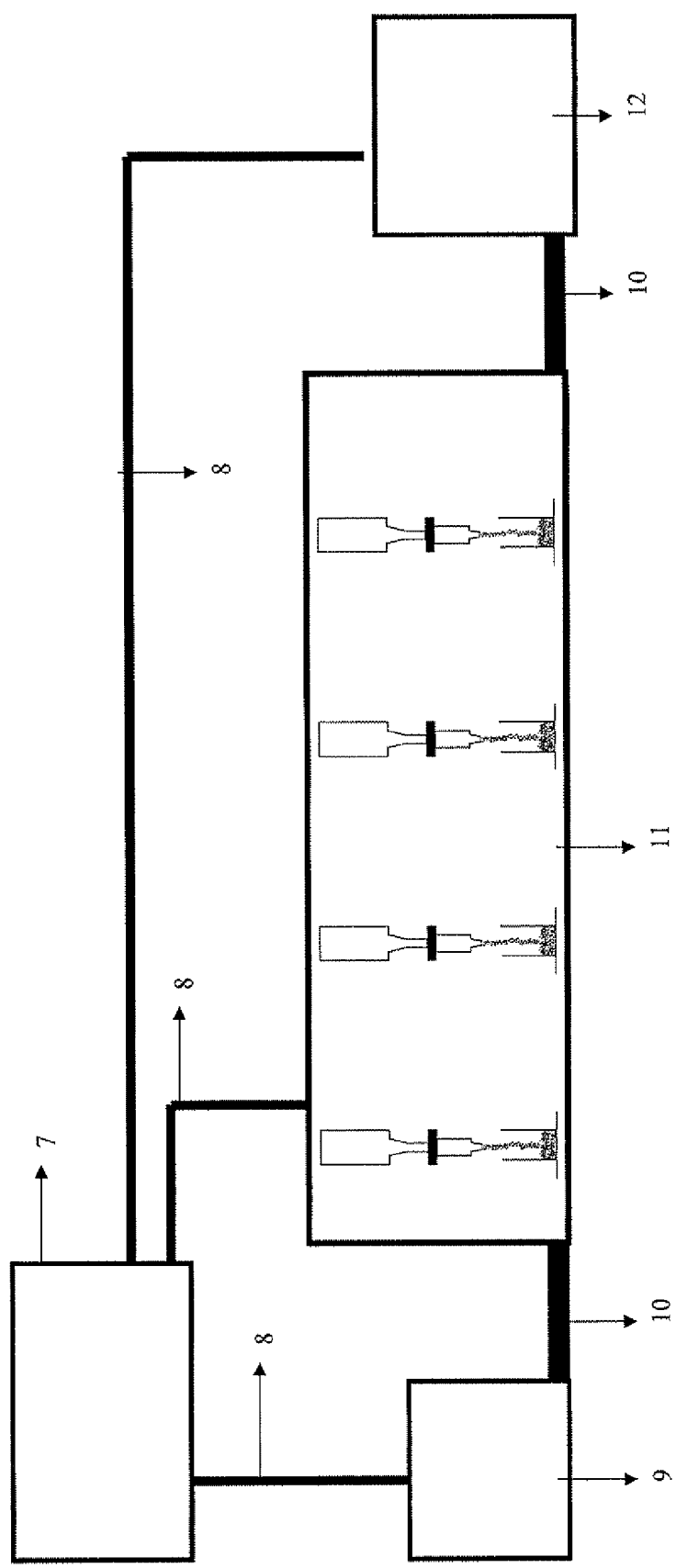
FIG. 2: Operational flow-chart documenting a system for preparing an individualized dosage form according to the invention.

Preferably, the production of the individualized dosage forms is undertaken in an automated and self-contained system as shown in the flow chart of FIG. 2. The system preferably has the following components:

1. A central computer control system having a processor that receives data relating to prescription and product requests from physicians, veterinarians, pharmacists and consumers. Requests from physicians and veterinarians are required for prescription drugs. Requests from consumers are sufficient for non-prescription medications, vitamins, mineral supplements and nutraceuticals. Requests can be received by electronic communications, facsimile transmissions, mail, courier services and personal delivery.

2. A first database stored on a computer readable medium that receives and stores the data from the processor on individual patients, their medicaments, desired dosage amounts and dosage times. Upon receipt of the requests, information such as the patient's or consumer's name and address, the physician or veterinarian's name and address, the required medicaments and desired amounts and times of dosing, the preference for capsule or a liquid or semi-solid product, the preferred choice of flavors and other information required by the appropriate regulations is recorded in the first database. The data entry sets up a reference file for that individual.

3. A second database stored on a computer readable medium that is in communication with the processor of the central computer control system and has data records associated with manufacturing inventory of medicaments, excipients and packaging materials.

4. A third database stored on a computer readable medium that is in communication with the processor and stores data associated with formulations of pellets, the pellets made of medicaments and excipients. The processor of the computer control system employs the information in the reference file and the third database to design a formulation, and uses the information in the second database to determine if the formulation components are present in the manufacturing inventory. If the components are present, then the processor takes the next steps to direct the manufacture, verification, consolidation, packaging, labeling and shipping of the requested dosage forms.

5. A mechanical transport system, preferably a robotic system, capable of moving formulation components such as pellets, capsule bodies, filled capsules, bottles, sachets and storage containers and that is in communication with the processor of the central computer control system such that in response to communication from the processor on the manufacturing inventory needed for a desired formulation of an individualized dosage form, the mechanical transport system transports the identified manufacturing inventory to the desired location. The mechanical transport system preferably also transports materials among the dispensing, verification and consolidation stations within the manufacturing system.

6. A storage system that in response to communications from the processor of the central computer system allocates and dispenses capsules, bottles, sachets, storage containers and shipping materials to the mechanical transport system to be delivered to the desired location in the system. Capsules or bottles are employed based on the requested preference for each individual patient.

7. One or more dispensing stations each associated with a single container of pellet formulation. Each container holds a pellet formulation containing a medicament or excipient. Capsules or bottles are independently transported and positioned under a series of the dispensing stations and filled with the designated amount of each pellet formulation. Control of the types and amount of the pellet formulations that are dispensed into a particular capsule or bottle is undertaken by the central computer system. Upon the completion of its designated filling cycle, the capsule or bottle contains a mixture of the required medicaments and excipients. Control of the amount of pellets dispensed can be undertaken via gravimetric or volumetric measurements. Under a gravimetric option, each dispensing station has a balance associated with it. The gravimetric or volumetric data documenting the amount of pellets that have been dispensed into a particular capsule or bottle are relayed to the central computer system for storage in a fourth database. The data is recorded for each assembled dosage unit and is associated with a unique code, such as a barcode, which is also associated with the final shipment container holding the dosage form. The code allows easy retrieval of manufacturing information.

8. One or more verification stations where the dosage forms are checked for the accuracy of the manufacturing process. The verification stations are in communication with the processor of the central computer system. Either or both of two techniques may be used for verification of the manufacturing process. The first technique matches the measured weight of the finished product against the sum of the weight of the capsule body or bottle and each weighing of the individual pellet formulations. The measured weight of the final product will have to be within a predetermined percentage of the calculated value of the sum of the weights. The second technique employs reflectance spectroscopy to verify the accuracy of the manufacturing process. The computer system calculates a projected proportional composite color profile based on the amount of each pellet formulation employed to manufacture each dosage unit. The measured color profile of each dosage unit has to be within a predetermined value of the calculated color profile.

9. One or more consolidation stations where the dosage units for an order are consolidated, packaged, labeled and made ready for shipment. The consolidation stations are controlled by the processor of the central computer system.

An individualized dosage form is prepared using the following steps:

1. For each dosage time, the computer system calculates the number of capsule bodies and caps or bottles required to manufacture the dosage forms. The calculations are based on the density of the pellet formulations, the required doses and the volume of the capsules and bottles. The storage system allocates the capsule bodies or bottles based on the input from the central computer system. The computer calculates the type and amount of pellets that are required to compile each dosage form. The computer computes the total projected weight of the formulation and the projected proportional color profile of the combined pellet formulations.
2. The robotic mechanical transfer system moves each capsule body or bottle to the requisite dispensing station in a sequence that is determined by the computer system. At each dispensing station, the capsule or bottle is weighed and the requisite amount of pellet formulation is added. The capsule or bottle is weighed again to determine the amount of pellet formulation that has been metered out at the station. The data is relayed to the computer system for storage in a fourth database.
3. At the end of the dispensing process, the accuracy of the manufacturing process is verified by measuring the combined total weight of the capsule body or bottle and the dispensed pellet formulations. The total weight has to be within a predetermined value of the projected weight calculated by the computer. The color profile of the pellet formulations used to manufacture the dosage form is measured by reflectance spectroscopy. The color profile has to be within a predetermined value of the projected color profile calculated by the computer. The verification data are relayed to the central computer system for storage in the fourth database.
4. After each capsule body or bottle has been filled with the requisite amounts of the various pellet formulations and the accuracy of the manufacturing process verified, it is sealed. In the case of a capsule, a cap is attached to the capsule body. Bottles containing materials for reconstitution into liquids or semi-solid formulations are sealed with tamper-proof caps. Capsules for a single dosing time are consolidated into a container that is sealed with a tamper-proof cap or into a sachet. Each consolidated container of capsules or bottle is labeled with the patient or consumer's name, the medicament contents and the date, time and instructions for the administration of the contents. Labels may be provided with specific color codes associated with the time of the day to further ensure patient compliance with administration instructions. For example, the container for capsules for administration prior to breakfast may be labeled with red, the container for capsules for administration with lunch may be labeled with yellow, etc. Upon request, labels may also be inscribed in Braille for patients whose sight is impaired. Each consolidated container of capsules or bottle is labeled with a barcode. The barcode allows for a convenient access to the manufacturing and composition records for each dosage form.
5. The containers for a requisite number of dosing times are then packaged in a shipment. The shipment is allocated a barcode and contains detailed information on the dosage forms contained therein. The barcode allows the shipment to be tracked. The barcode is also associated with a unique data record that documents the details of the pellet formulations and manufacturing process employed to assemble each particular capsule and bottle contained within the shipment.

EXAMPLES

Example 1

This example concerns two patients with the following profiles:

Patient 1 is a 60-year-old female weighing 70 kG with a renal clearance of 90 mL/minute. She is capable of swallowing capsules. She is being treated for post-menopausal osteoporosis, hypertension, cholesterol control and arthritis pain relief, and also receives multivitamins and calcium supplements.

Patient 2 is a 70-year-old female weighing 50 kG suffering from renal insufficiency with a renal clearance of 30 mL/minute. She is not capable of easily swallowing capsules and would prefer liquid formulations. She is being treated for the prevention of post-menopausal osteoporosis, hypertension, heart failure, cholesterol control, and arthritis pain, and also receives maintenance therapy for duodenal ulcer, multivitamins and calcium supplements.

The physician's medication orders for the two patients involving an initial and maintenance-dosing regimen for a 30-day period are as follows:

| Patient 1 | | |
|---|---|---|
| Enalapril 5 mg | 90 tablets | 1.5 tablets twice a day |
| Ibuprofen 400 mg | 120 tablets | 1 tablet four times a day |
| Lovastatin 20 mg | 7 tablets | 1 tablet daily post-evening meal Day 1-7 followed by, |
| Lovastatin 50 mg | 23 tablets | 1 tablet daily post-evening meal |
| Alendronate 10 mg | 30 tablets | 1 tablet daily once a day |

At the suggestion of her physician, the patient also requests the following from her pharmacist:

| Calcium supplement tablets | 500 mg twice a day |
|---|---|
| Multivitamin supplement tablets | Once a day |

| Patient 2 | | |
|---|---|---|
| Enalapril 10 mg | 90 tablets | 1.5 tablets twice a day |
| Celecoxib 100 mg | 90 capsules | 150 mg orally twice a day |
| Lovastatin 20 mg | 7 tablets | 1 tablet daily post-evening meal Day 1-7 followed by, |
| Lovastatin 50 mg | 23 tablets | 1 tablet daily post-evening meal |
| Digoxin 187.5 mcg | Use Oral liquid | Once a day |
| Cimetidine 150 mg | Use Oral liquid | Once a day |
| Alendronate 5 mg | 30 tablets | 1 tablet daily |

At the suggestion of her physician, the patient also requests the following from her pharmacist preferably in a liquid form:

| Calcium supplement | 500 mg orally twice a day |
|---|---|
| Multivitamin supplement | Orally once a day |

The patient's physician suggests that the multivitamin doses be administered at a third of the normal dosage.

With the typical commercial products presently available, the pharmacist provides the medications to the patients in the following fashion:

For Patient 1 in seven bottles:

| | |
|---|---|
| 5 mg Enalapril maleate | 90 tablets |
| 400 mg Ibuprofen | 120 tablets |
| 20 mg Lovastatin | 7 tablets |
| 50 mg Lovastatin | 23 tablets |
| 10 mg Alendronate sodium | 30 tablets |
| 200 mg calcium citrate | 150 tablets |
| Multivitamins | 30 tablets |

Patient 1 or a healthcare provider has to undertake the following allocation of the products for administration:

Patient 1: Day 1 to 7

| | Number of tablets administered at dosing time | | | | |
|---|---|---|---|---|---|
| Medication | Early morning | Morning meal | Midday meal | Evening meal | Bedtime |
| 5 mg Enalapril maleate | | 1.5 | | 1.5 | |
| 400 mg Ibuprofen | | 1 | 1 | 1 | 1 |
| 20 mg Lovastatin | | | | 1 | |
| 10 mg Alendronate sodium | 1 | | | | |
| 200 mg Calcium citrate | | 2.5 | | 2.5 | |
| Multivitamin[a] | | 1 | | | |

Patient 1: Day 8 to 30

| | Number of tablets administered at dosing time | | | | |
|---|---|---|---|---|---|
| Medication | Early morning | Morning meal | Midday meal | Evening meal | Bedtime |
| 5 mg Enalapril maleate | | 1.5 | | 1.5 | |
| 400 mg Ibuprofen | | 1 | 1 | 1 | 1 |
| 50 mg Lovastatin | | | | 1 | |
| 10 mg Alendronate sodium | 1 | | | | |
| 200 mg Calcium citrate | | 2.5 | | 2.5 | |
| Multivitamin[a] | | 1 | | | |

[a]Contains Vitamin A, Vitamin $D_2$, Vitamin E, Vitamin C, Thiamine, Riboflavin, Niacinamide, Pyridoxine and Vitamin $B_{12}$ For Patient 2 in nine bottles:

| | |
|---|---|
| 10 mg Enalapril maleate | 90 tablets |
| 100 mg Celecoxib | 90 capsules |
| 20 mg Lovastatin | 7 tablets |
| 50 mg Lovastatin | 23 tablets |
| Digoxin | 112.5 ml of a 50 mcg/ml liquid |
| Cimetidine | 237 ml of a 60 mg/ml liquid |
| 5 mg Alendronate sodium | 30 tablets |
| 500 mg Calcium citrate | 60 effervescent tablets |
| Multivitamins | 237 ml of a liquid formulation |

The pharmacist discusses the Celecoxib situation with the physician. The product is available in 100 mg capsules. The capsules cannot be subdivided. Consequently, a 150 mg dose cannot be administered. The physician requests that the total daily dose of 300 mg be divided into two doses of 100 mg and 200 mg each.

Patient 2 or a healthcare provider has to undertake the following allocation of the products for administration:

Patient 2: Day 1 to 7

| | Amounts administered at dosing time | | | | |
|---|---|---|---|---|---|
| Medication | Early morning | Morning meal | Midday meal | Evening meal | Bedtime |
| 10 mg Enalapril maleate tablet | | 1.5 | | 1.5 | |
| 100 mg Celecoxib capsules | | 2 | | 1 | |
| 20 mg Lovastatin tablets | | | | 1 | |
| 50 mcg/ml Digoxin liquid | | 3.75 ml | | | |
| 60 mg/ml Cimetidine liquid | | | | | 2.5 ml |
| 5 mg Alendronate sodium tablet | 1 | | | | |
| 500 mg Calcium citrate tablets | | 1[a] | | 1[a] | |
| Multivitamin liquid | | 5 ml[b] | | | |

Patient 2: Day 7 to 30

| | Amounts administered at dosing time | | | | |
|---|---|---|---|---|---|
| Medication | Early morning | Morning meal | Midday meal | Evening meal | Bedtime |
| 10 mg Enalapril maleate tablet | | 1.5 | | 1.5 | |
| 100 mg Celecoxib capsules | | 2 | | 1 | |
| 50 mg Lovastatin tablets | | | | 1 | |
| 50 mcg/ml Digoxin liquid | | 3.75 ml | | | |
| 60 mg/ml Cimetidine liquid | | | | | 2.5 ml |
| 5 mg Alendronate sodium tablet | 1 | | | | |
| 500 mg Calcium citrate tablets | | 1[a] | | 1[a] | |
| Multivitamin liquid | | 5 ml[b] | | | |

[a]Administered as a liquid formula made from the effervescent tablet
[b]Contains Vitamin A, Vitamin D, Vitamin E, Vitamin C, Thiamine, Riboflavin, Niacin, Vitamin $B_6$ and Vitamin $B_{12}$.

The use of presently available commercial products leads to the following disadvantages:
1. For Patient 1, the commercial products involve the allocation of up to fifteen tablets daily and subdivision of tablets.
2. For Patient 2, the products involve the allocation and subdivision of up to ten tablets and capsules, the reconstitution of an effervescent tablet into a liquid formulation and the allocation of three liquid formulation doses.
3. For Patient 2, the dose for celecoxib cannot be divided into equal parts of 150 mg each.
4. To achieve the desired liquid dosing protocol for Patient 2, a liquid formulation will have to be prepared from the tablets and capsules. This will involve grinding of the tablets into a powder and the opening and removal of the contents of the capsules. The combined powders will then have to be reconstituted into a liquid formulation and adequately flavored and sweetened. The compounding process may have to be undertaken without any detailed information on the potential physical-chemical, taste and odor characteristics of the resultant liquid product. Therefore, the formulated liquid products may provide less than the desired dose of the active ingredients due to chemical decomposition. Patient compliance may also be compromised due to less than desirable taste and odor characteristics. The pharmacist may not agree to undertake such a compounding procedure, leaving it to be performed by the patient or caregiver.

The following products are manufactured according to the invention to provide the medication requirements for the two patients:

Patient 1: Day 1 to 7

| | Encapsulated packaged products for dosing times | | | | |
|---|---|---|---|---|---|
| Medication | Early morning | Morning meal | Midday meal | Evening meal | Bedtime |
| Enalapril maleate | | 7.5 mg | | 7.5 mg | |
| Ibuprofen | | 400 mg | 400 mg | 400 mg | 400 mg |
| Lovastatin | | | | 20 mg | |
| Alendronate sodium | 10 mg | | | | |
| Calcium citrate | | 500 mg | | 500 mg | |
| Vitamin A | | 5000 International Units | | | |
| Vitamin D$_2$ | | 400 International Units | | | |
| Vitamin E | | 30 International Units | | | |
| Vitamin C | | 120 mg | | | |
| Thiamine | | 3 mg | | | |
| Riboflavin | | 3 mg | | | |
| Niacinamide | | 25 mg | | | |
| Pyridoxine | | 2 mg | | | |
| Vitamin B$_{12}$ | | 6 mg | | | |

Patient 1: Day 8 to 30

| | Encapsulated packaged products for dosing times | | | | |
|---|---|---|---|---|---|
| Medication | Early morning | Morning meal | Midday meal | Evening meal | Bedtime |
| Enalapril maleate | | 7.5 mg | | 7.5 mg | |
| Ibuprofen | | 400 mg | 400 mg | 400 mg | 400 mg |
| Lovastatin | | | | 50 mg | |
| Alendronate sodium | 10 mg | | | | |
| Calcium citrate | | 500 mg | | 500 mg | |
| Vitamin A | | 5000 International Units | | | |
| Vitamin D$_2$ | | 400 International Units | | | |
| Vitamin E | | 30 International Units | | | |
| Vitamin C | | 120 mg | | | |
| Thiamine | | 3 mg | | | |
| Riboflavin | | 3 mg | | | |
| Niacinamide | | 25 mg | | | |
| Pyridoxine | | 2 mg | | | |
| Vitamin B$_{12}$ | | 6 mg | | | |

1. The above products are supplied in capsules. The capsules contain a mixture of medicaments such that at each dosage time one capsule or integral multiples of one capsule are administered. Also, the capsules are provided to the patient in labeled containers so all the patient has to do is identify the container with the current weekday and dosage time then take all of the capsules packaged in the container. No further allocation by patient or caregiver is required.
2. The capsules are administered with an appropriate quantity of a suitable fluid.
3. The early morning dose is to be administered at least one half hour prior to the first food intake of the day. The product is to be administered with water.

Patient 2: Day 1 to 7

| | Products packaged in a bottle for dosing times | | | | |
|---|---|---|---|---|---|
| Medication | Early morning | Morning meal | Midday meal | Evening meal | Bedtime |
| Enalapril maleate | | 15 mg | | 15 mg | |
| Celecoxib | | 150 mg | | 150 mg | |
| Lovastatin | | | | 20 mg | |
| Digoxin | | 187.5 mcg | | | |
| Cimetidine | | | | | 150 mg |
| Alendronate sodium | 5 mg | | | | |
| Calcium citrate | | 500 mg | | 500 mg | |
| Vitamin A | | 1667 International Units | | | |
| Vitamin D$_2$ | | 133 International Units | | | |
| Vitamin E | | 10 International Units | | | |
| Vitamin C | | 40 mg | | | |
| Thiamine | | 1 mg | | | |
| Riboflavin | | 1 mg | | | |
| Niacinamide | | 8.3 mg | | | |
| Pyridoxine | | 0.7 mg | | | |
| Vitamin B$_{12}$ | | 2 mg | | | |
| Modified corn starch | | 300 mg | 300 mg | 300 mg | 300 mg |
| Sweetened vanilla flavor powder | | 600 mg | 600 mg | 600 mg | 600 mg |
| Sweetened orange flavor powder | | 500 mg | 500 mg | 500 mg | 500 mg |

Patient 2: Day 8 to 30

| | Products packaged in a bottle for dosing times | | | | |
|---|---|---|---|---|---|
| Medication | Early morning | Morning meal | Midday meal | Evening meal | Bedtime |
| Enalapril maleate | | 15 mg | | 15 mg | |
| Celecoxib | | 150 mg | | 150 mg | |
| Lovastatin | | | | 50 mg | |
| Digoxin | | 187.5 mcg | | | |
| Cimetidine | | | | | 150 mg |
| Alendronate sodium | 5 mg | | | | |
| Calcium citrate | | 500 mg | | 500 mg | |
| Vitamin A | | 1667 International Units | | | |
| Vitamin D$_2$ | | 133 International Units | | | |
| Vitamin E | | 10 International Units | | | |

-continued

| Medication | Products packaged in a bottle for dosing times | | | | |
|---|---|---|---|---|---|
| | Early morning | Morning meal | Midday meal | Evening meal | Bedtime |
| Vitamin C | | 40 mg | | | |
| Thiamine | | 1 mg | | | |
| Riboflavin | | 1 mg | | | |
| Niacinamide | | 8.3 mg | | | |
| Pyridoxine | | 0.7 mg | | | |
| Vitamin $B_{12}$ | | 2 mg | | | |
| Modified corn starch | 300 mg | 300 mg | 300 mg | 300 mg | 300 mg |
| Sweetened vanilla flavor powder | | 600 mg | 600 mg | 600 mg | 600 mg |
| Sweetened orange flavor powder | | 500 mg | 500 mg | 500 mg | 500 mg |

1. For each dosing time, the above products are supplied as pellets of small diameter size in a single bottle.
2. The pellets of small diameter size are reconstituted into a flavored liquid by the addition of 15 ml of water to the bottle and shaking the contents.
3. The early morning dose is to be administered at least one half hour prior to the first food intake of the day.

In contrast to the commercially available products, the formulations designed according to the invention accomplish all of the following objectives:

1. The formulations can be dosed without the need for allocation, subdivision or major compounding operations by the patient or the patient's caregiver.
2. The formulations are produced for administration according to the individual preferences of each patient. In the above examples, the products are formulated for dosing as capsules or flavored oral liquids. This leads to easier dosing procedures, better patient compliance and enhanced therapeutic benefits
3. Where required, the invention allows the doses of the medications to be easily adjusted for physiological characteristics and the consumer's preferences in the case of nutritional supplements. In the examples above the doses of enalapril maleate, cimetidine and digoxin are adjusted for renal clearance. The dose of celecoxib can be administered as per the exact recommendations of the physician. The dose of vitamins is adjusted to suit consumer preferences.
4. Each dosage form for a specific dosing time is labeled with unique administration instructions for the enclosed medications.

Example 2

The second example concerns two feline patients.

The first patient weighs 3.6 kg and is being treated for an infection and general allergies. The preferred dosing method for the patient is a flavored viscous liquid. The patient's owner suggests a fish flavored product.

The second patient weighs 6.8 kg and is being treated for an infection and general allergies. The preferred dosing method for the patient is a flavored viscous liquid. The patient's owner suggests a chicken flavored product.

The veterinarian's prescription for a 14-day period for the two patients is as follows:

| Patient 1 | |
|---|---|
| Amoxicillin | 6.6 mg/kg orally thrice a day |
| Pseudoephedrine | 7.5 mg orally twice a day |

Adjust amoxicillin dosage for a body weight of 3.6 kg.

If possible, provide product as a liquid flavored as per patient owner's preference.

| Patient 2 | |
|---|---|
| Amoxicillin | 6.6 mg/kg orally thrice a day |
| Pseudoephedrine | 7.5 mg orally twice a day |

Adjust amoxicillin dosage for a body weight of 6.8 kg.

If possible, provide product as a liquid flavored as per patient owner's preference.

With the typical commercial products presently available, the pharmacist provides the medications to the patients in the following fashion:

For Patient 1 in two bottles:

| Amoxicillin liquid | 30 ml of a 50 mg/ml product |
|---|---|
| Pseudoephedrine liquid | 119 ml of a 6 mg/ml product |

Patient 2 in three bottles:

| Amoxicillin liquid | 45 ml of a 50 mg/ml product |
|---|---|
| Pseudoephedrine liquid | 119 ml of a 6 mg/ml product |

The patient's owner has to undertake the following allocation of the products for administration:

Patient 1: Day 1 to 14

| | Amounts administered at dosing time | | |
|---|---|---|---|
| Medication | Morning | Midday | Evening |
| 50 mg/ml Amoxicillin liquid | 0.5 ml | 0.5 ml | 0.5 ml |
| 6 mg/ml Pseudoephedrine liquid | 1.25 ml | | 1.25 ml |

Patient 2: Day 1 to 14

| | Amounts administered at dosing time | | |
|---|---|---|---|
| Medication | Morning | Midday | Evening |
| 50 mg/ml Amoxicillin liquid | 0.9 ml | 0.9 ml | 0.9 ml |
| 6 mg/ml Pseudoephedrine liquid | 1.25 ml | | 1.25 ml |

The use of commercial products leads to the following disadvantages:

1. The flavor and viscosity of the products do not meet the patient's preferences. For example, the pseudoephedrine product is designed for human patients.
2. A compounding operation will have to be undertaken to flavor the product. The compounding process may have to be undertaken without any detailed information on the physical-chemical, taste and odor characteristics of the resultant liquid product. Therefore, the formulated liquid products may provide less than the desired dose of the active ingredients due to chemical decomposition. The ability to easily dose the product and the resultant patient compliance may be compromised due to less than desirable taste, odor and viscosity characteristics. This would cause inconvenience to the owners of the patient and less than ideal therapeutic benefits to the patient. The pharmacist may or may not agree to undertake such a compounding procedure.

The following products are manufactured according to the invention to provide the medication requirements for the two patients:

Patient 1: Day 1 to 14

| Medication/Excipients | Products packaged in a single bottle for each dosing time | | |
|---|---|---|---|
| | Morning | Midday | Evening |
| Amoxicillin | 24 mg | 24 mg | 24 mg |
| Pseudoephedrine | 7.5 mg | | 7.5 mg |
| Modified corn starch | 150 mg | 150 mg | 150 mg |
| Dried salmon flavor | 250 mg | 250 mg | 250 mg |

Patient 2: Day 1 to 14

| Medication/Excipients | Products packaged in a single bottle for each dosing time | | |
|---|---|---|---|
| | Morning | Midday | Evening |
| Amoxicillin | 45 mg | 45 mg | 45 mg |
| Pseudoephedrine | 7.5 mg | | 7.5 mg |
| Modified corn starch | 150 mg | 150 mg | 150 mg |
| Dried chicken flavor | 250 mg | 250 mg | 250 mg |

1. The above products are supplied in a bottle as pellets of small diameter size.
2. The pellets of small diameter size are reconstituted into a flavored viscous liquid product by the addition of 10 ml of water to the bottle and shaking the contents.
3. The dose can be administered to the patient via an oral syringe or by addition to the patient's food.

In contrast to the commercially available products, the formulations designed according to the invention are produced according to the preferences of the owner of each patient. The objectives are achieved employing an automated and well-controlled technique without the involvement of the patient's owners or healthcare providers in the allocation or compounding of the medications. In this example, the formulations of amoxicillin and pseudoephedrine are produced as viscous oral liquids flavored according to the preferences of the patient's owner. This leads to easier dosing procedures, better patient compliance and enhanced therapeutic benefits.

Example 3

The third example concerns two canine patients.

The first patient weighs 6.75 kg and is being treated for a cardiac disease. The preferred dosing method for the patient is a flavored viscous liquid. The patient's owner suggests a beef and bacon flavored product.

The second patient weighs 22.5 kg and is being treated for a cardiac disease. The preferred dosing method for the patient is a flavored viscous liquid. The patient's owner suggests a chicken flavored product.

The veterinarian's prescription for a 30 day period for the two patients is as follows:

| Patient 1 | |
|---|---|
| Furosemide | 4.4 mg/kg orally twice a day |
| Digoxin | 0.6 mcg/kg mg orally twice a day |

Adjust dosages for a body weight of 6.75 kg.

If possible, provide product as a liquid flavored as per patient owner's preference.

| Patient 2 | |
|---|---|
| Furosemide | 4.4 mg/kg orally twice a day |
| Digoxin | 0.6 mcg/kg orally twice a day |

Adjust dosage for a body weight of 22.5 kg.

If possible, provide product as a liquid flavored as per patient owner's preference.

With the typical commercial products presently available, the pharmacist provides the medications to the patients in the following fashion:

For Patient 1 in two bottles:

| 50 mg Furosemide | 30 tablets |
|---|---|
| 0.05 mg/ml Digoxin liquid | 60 ml |

Patient 2 in two bottles:

| 50 mg Furosemide | 120 tablets |
|---|---|
| 0.15 mg/ml Digoxin liquid | 60 ml |

The pharmacist discusses the dosing of furosemide dose for Patient 1 with the veterinarian. The required dose is 30 mg. However, subdivision of the 50 mg tablet can only be undertaken into two approximately equal parts to provide a 25 mg dose. The veterinarian agrees to a dose of 25 mg.

The patient's owner has to undertake the following allocation of the products for administration:

Patient 1: Day 1 to 30

|  | Amounts administered at dosing time | |
|---|---|---|
| Medication | Morning | Evening |
| 50 mg Furosemide tablets | 0.5 tablet | 0.5 tablet |
| 0.05 mg/ml Digoxin liquid | 0.8 ml | 0.8 ml |

Patient 2: Day 1 to 30

|  | Amounts administered at dosing time | |
|---|---|---|
| Medication | Morning | Evening |
| 50 mg Furosemide tablets | 2 tablets | 2 tablets |
| 0.15 mg/ml Digoxin liquid | 0.9 ml | 0.9 ml |

The use of commercial products leads to the following disadvantages:

1. The furosemide dose for Patient 1 cannot be dosed at an optimal level for therapeutic benefit.
2. The above products are not formulated and flavored for the patient's preferences. A compounding operation will have to be undertaken to grind the tablet and to prepare a flavored liquid product. The compounding process may have to be undertaken without any detailed information on the physical-chemical, taste and odor characteristics of the resultant liquid product. Therefore, the formulated liquid products may provide less than the desired dose of the active ingredients due to chemical decomposition. The ability to easily dose the product and the resultant patient compliance may be compromised due to less than desirable taste, odor and viscosity characteristics. This would cause inconvenience to the owners of the patient and less than ideal therapeutic benefits to the patient. The pharmacist may or may not agree to undertake such a compounding procedure.

The following products are manufactured according to the invention to provide the medication requirements for the two patients:

Patient 1: Day 1 to 30

|  | Products packaged in a single bottle for dosing times | |
|---|---|---|
| Medication/Excipients | Morning | Evening |
| Furosemide | 30 mg | 30 mg |
| Digoxin | 0.041 mg | 0.041 mg |
| Modified corn starch | 150 mg | 150 mg |
| Dried beef flavor | 200 mg | 200 mg |
| Dried bacon flavor | 100 mg | 100 mg |

Patient 2: Day 1 to 14

|  | Products packaged in a single bottle for each dosing time | |
|---|---|---|
| Medication/Excipients | Morning | Evening |
| Furosemide | 99 mg | 99 mg |
| Digoxin | 0.135 mg | 0.135 mg |
| Modified corn starch | 150 mg | 150 mg |
| Dried chicken flavor | 300 mg | 300 mg |

1. The above products are supplied in a bottle as pellets of small diameter size.
2. The pellets of small diameter size are reconstituted into a flavored viscous liquid product by the addition of 10 ml of water to the bottle and shaking the contents.
3. The dose can be administered to the patient via an oral syringe or by addition to the patient's food.

In contrast to the commercially available products, the formulations designed according to the invention for the two patients accomplish all of the following objectives:

1. The formulations are produced for administration according to the preferences of the owner of each patient. In the above example the products are dosed as viscous liquids flavored according to the preferences of the patient's owner. This leads to easier dosing procedures, better patient compliance and enhanced therapeutic benefits
2. The invention allows the doses of the medications to be easily adjusted for body weight as per the instructions of the patient's veterinarian. The doses of furosemide and digoxin are easily adjusted for the body weight of the patient.

I claim:

1. A method to prepare an individualized dosage form of a medicament, the method comprising:
   (a) receiving information identifying for an individual patient the medicament and a desired dosage amount at a dosage time of the medicament desired for therapeutic effect;
   (b) selecting at least two pellets comprising the medicament; and
   (c) combining the pellets into a single capsule to prepare an individualized dosage form that alone or in integral multiples provides the desired dosage amount for the individual patient at the dosage time.

2. The method of claim 1 that is repeated until individualized dosage forms are prepared to provide for each dosage time in one day for the medicament that is desired for therapeutic effect for the individual patient.

3. The method of claim 1, wherein the method is repeated to prepare individualized dosage forms for at least two individual patients.

4. The method of claim 1 wherein the information identifies for the individual patient a first and a second medicament and their respective desired dosage amounts for administration at a single dosage time desired for therapeutic effect, the pellets comprise a first pellet comprised of the first medicament and a second pellet comprised of the second medicament, and the pellets are combined into a single capsule that alone or in integral multiples provides the desired dosage amount for the individual patient of the first and second medicaments at the single dosage time.

5. The method of claim 4 that is repeated until individualized dosage forms are prepared for each dosage time in one day for the first and second medicaments that is desired for therapeutic effect for the individual patient.

6. The method of claim 1 wherein the medicament is selected from the group consisting of prescription medications and nutritional supplements.

7. The method of claim 1 wherein the pellets comprise at least one pellet comprising a medicament and at least one pellet comprising an excipient.

8. The method of claim 7 wherein the pellets comprise at least one pellet comprising a medicament and having a coating that gradually erodes upon exposure to aqueous environments and at least one pellet comprising an excipient and having a coating that rapidly erodes upon exposure to aqueous environments.

9. A method to prepare an individualized dosage form of a medicament for reconstitution into a liquid, the method comprising:
(a) receiving information identifying for an individual patient the medicament and a desired dosage amount at a dosage time of the medicament desired for therapeutic effect;
(b) selecting pellets comprising the medicament and an excipient, wherein if the medicament and the excipient are contained in one pellet, at least two pellets are selected and if the medicament and the excipient are contained in separate pellets, at least one medicament pellet and at least one excipient pellet are selected, further wherein the pellets are dispersible in the liquid at room temperature with agitation; and
(c) combining the pellets into a single container to prepare an individualized dosage form; and
(d) packaging the single container with instructions to add the liquid to the contents of the single container sufficient to prepare a liquid individualized dosage form.

10. The method of claim 9 that is repeated until individualized dosage forms are prepared to provide for each dosage time in one day for the medicament that is desired for therapeutic effect for the individual patient.

11. The method of claim 9, wherein the method is repeated to prepare individualized dosage forms for at least two individual patients.

12. The method of claim 9 wherein the information identifies for the individual patient a first and a second medicament and their respective desired dosage amounts for administration at a single dosage time desired for therapeutic effect, the pellets comprise a first pellet comprised of the first medicament and a second pellet comprised of the second medicament, and the pellets are combined into the single container that provides the desired dosage amount for the individual patient of the first and the second medicaments at the single dosage time.

13. The method of claim 12 that is repeated until individualized dosage forms are prepared for each dosage time in one day for the first and second medicaments that is desired for therapeutic effect for the individual patient.

14. The method of claim 9 wherein the medicament is selected from the group consisting of prescription medications and nutritional supplements.

15. A system for preparing an individualized dosage form comprising:
(a) a first database stored on a computer readable medium having data records associated with an individual patient and containing information on a medicament, its desired dosage amount and dosage time for the individual patient;
(b) a second database stored on a computer readable medium having data records associated with manufacturing inventory of medicaments, excipients and packaging materials;
(c) a third database stored on a computer readable medium having data records associated with capsule formulations of pellets, said pellets comprised of medicaments and excipients;
(d) a processor associated with the first, second and third databases that is configured to identify a capsule formulation of pellets that alone or in integral multiples provides the desired dosage amount for the individual patient at the dosage time and that is further configured to identify manufacturing inventory needed to prepare the capsule formulation;
(e) a mechanical transport system that is in communication with the processor and that, in response to communication from the processor on the manufacturing inventory needed to prepare the capsule formulation, transports the identified manufacturing inventory from a storage area; and
(f) a dispensing station that receives the identified manufacturing inventory from the mechanical transport system, wherein the dispensing station is in communication with the processor such that information on the capsule formulation is received by the dispensing station and the dispensing station dispensing pellets into a capsule body in a quantity and amount such that an individualized dosage form that alone or in integral multiples provides the desired dosage amount of the medicament for the individual patient at a single dosage time is prepared.

16. The system of claim 15 further comprising a verification station in communication with the processor that analyzes the individualized dosage form to verify that the form contains desired components in desired amounts.

17. The system of claim 16 wherein the verification station comprises (i) a balance; (ii) a dosage color profile analyzer for reflectance spectroscopy; or (iii) both a balance and a dosage color profile analyzer for reflectance spectroscopy.

18. The system of claim 16 still further comprising a consolidating station in communication with the processor, wherein in the consolidating station multiple individualized dosage forms for a single dosing time for the individual patient are consolidated and packaged together in one container that is sealed and labeled with a barcode.

19. The system of claim 18 wherein the consolidating station consolidates multiple individualized dosage forms for more than one dosing time for the individual patient into one shipment labeled with a barcode.

20. A system for preparing an individualized dosage form for reconstitution into a liquid comprising:
(a) a first database stored on a computer readable medium having data records associated with an individual patient and containing information on a medicament, its desired dosage amount and dosage time for the individual patient;
(b) a second database stored on a computer readable medium having data records associated with manufacturing inventory of medicaments, excipients and packaging materials;
(c) a third database stored on a computer readable medium having data records associated with formulations of pellets for reconstitution in the liquid, said pellets comprised of medicaments and excipients;
(d) a processor associated with the first, second and third databases that is configured to identify a formulation of pellets for reconstitution in the liquid that provides the desired dosage amount for the individual patient at the dosage time and that is further configured to identify manufacturing inventory needed to prepare the formulation;

(e) a mechanical transport system that is in communication with the processor and that, in response to communication from the processor on the manufacturing inventory needed to prepare the formulation, transports the identified manufacturing inventory from a storage area; and (f) a dispensing station that receives the identified manufacturing inventory from the mechanical transport system, wherein the dispensing station is in communication with the processor such that information on the formulation is received by the dispensing station and the dispensing station dispensing pellets into a single container in a quantity and amount such that an individualized dosage form that provides the desired dosage amount of the medicament for the individual patient at the single dosage time is prepared; and (g) a consolidating station in communication with the processor that receives the single container comprising the individualized dosage form, packages the container with written instructions to add the liquid to the contents of the single container sufficient to prepare a liquid individualized dosage form and labels the container with a barcode.

21. The system of claim 20 further comprising a verification station in communication with the processor that analyzes the individualized dosage form to verify that the form contains desired components in desired amounts.

22. The system of claim 21 wherein the verification station comprises (i) a balance; (ii) a dosage color profile analyzer for reflectance spectroscopy; or (iii) both a balance and a dosage color profile analyzer for reflectance spectroscopy.

23. The system of claim 22 wherein the consolidating station consolidates multiple individualized dosage forms for more than one dosing time for the individual patient into one shipment labeled with a barcode.

* * * * *

UNITED STATES PATENT AND TRADEMARK OFFICE
CERTIFICATE OF CORRECTION

PATENT NO. : 7,457,685 B2  Page 1 of 1
APPLICATION NO. : 10/578120
DATED : November 25, 2008
INVENTOR(S) : Joe D'Silva It is certified that error appears in the above-identified patent and that said Letters Patent is hereby corrected as shown below:

On the Title page item (54), and col. 1, line 1, should be changed from

"Preparing For Indiv idualized Dosage Forms of Medicaments"

to

-- Preparing Individualized Dosage Forms of Medicaments --.

Signed and Sealed this

Seventeenth Day of February, 2009

JOHN DOLL
*Acting Director of the United States Patent and Trademark Office*